(12) United States Patent
Schneider et al.

(10) Patent No.: US 12,161,374 B2
(45) Date of Patent: *Dec. 10, 2024

(54) MATRIX IMPLANT

(71) Applicant: SI-Bone Inc., Santa Clara, CA (US)

(72) Inventors: Bret W. Schneider, San Jose, CA (US); Roxanne Simon, San Jose, CA (US); Derek P. Lindsey, San Jose, CA (US); Scott A. Yerby, Montara, CA (US)

(73) Assignee: SI-Bone Inc., Santa Clara, CA (US)

( * ) Notice: Subject to any disclaimer, the term of this patent is extended or adjusted under 35 U.S.C. 154(b) by 352 days.

This patent is subject to a terminal disclaimer.

(21) Appl. No.: 17/443,388

(22) Filed: Jul. 26, 2021

(65) Prior Publication Data

US 2022/0117640 A1   Apr. 21, 2022

Related U.S. Application Data

(63) Continuation of application No. 16/263,971, filed on Jan. 31, 2019, now Pat. No. 11,071,573, which is a
(Continued)

(51) Int. Cl.
*A61B 17/84* (2006.01)
*A61B 17/70* (2006.01)
(Continued)

(52) U.S. Cl.
CPC .......... *A61B 17/84* (2013.01); *A61B 17/7055* (2013.01); *A61F 2/44* (2013.01);
(Continued)

(58) Field of Classification Search
CPC .... A61B 17/7055; A61F 2/4455; A61F 2/447; A61F 2002/0912; A61F 2002/30308;
(Continued)

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

Sand et al.; U.S. Appl. No. 17/447,550 entitled "Systems and methods for decorticating the sacroloac joint," filed Sep. 13, 2021.
ACUMED; Acutrak Headless Compressioin Screw (product information); 12 pgs; © 2005; retrieved Sep. 25, 2014 from http://www.rcsed.ac.uk/fellows/lvanrensburg/classification/surgtech/acumed/manuals/acutrak-brochure%200311.pdf.
(Continued)

*Primary Examiner* — Ellen C Hammond
(74) *Attorney, Agent, or Firm* — Shay Glenn LLP

(57) ABSTRACT

Implants for the fusion or fixation of two bone segments are described. For example, the implants can be used for the fusion or fixation of the sacroiliac joint. The implants can have a matrix structure, have a rectilinear cross-sectional area, and have a curvature.

18 Claims, 10 Drawing Sheets

Related U.S. Application Data continuation of application No. 15/593,208, filed on May 11, 2017, now Pat. No. 10,194,962, which is a continuation of application No. 14/859,005, filed on Sep. 18, 2015, now Pat. No. 9,662,157.

(60) Provisional application No. 62/052,379, filed on Sep. 18, 2014.

(51) Int. Cl.
  *A61F 2/44* (2006.01)
  *A61F 2/28* (2006.01)
  *A61F 2/30* (2006.01)

(52) U.S. Cl.
  CPC .......... *A61F 2002/2839* (2013.01); *A61F 2002/30115* (2013.01); *A61F 2002/30149* (2013.01); *A61F 2002/30154* (2013.01); *A61F 2002/30156* (2013.01); *A61F 2002/30171* (2013.01); *A61F 2002/30604* (2013.01); *A61F 2002/30995* (2013.01); *A61F 2002/4495* (2013.01)

(58) Field of Classification Search
  CPC .......... A61F 2002/3028–30281; A61F 2002/30273–30276; A61F 2002/30995
  See application file for complete search history.

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |

(56) References Cited

U.S. PATENT DOCUMENTS

| | | |
|---|---|---|
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,436,139 B1 | 8/2002 | Shapiro et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,551,343 B1 | 4/2003 | Törmälii et al. |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 * | 5/2009 | Branch ............... A61F 2/446 623/17.11 |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 7,951,176 B2 | 5/2011 | Grady et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,257,398 B2 | 9/2012 | Jackson |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,398,682 B2 | 3/2013 | Jackson et al. |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,597,299 B2 | 12/2013 | Farr et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |

(56) References Cited

U.S. PATENT DOCUMENTS

| | | |
|---|---|---|
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,788,961 B2 | 10/2017 | Donner et al. |
| 9,808,298 B2 | 11/2017 | Stroncek et al. |
| 9,808,299 B2 | 11/2017 | Goel et al. |
| 9,808,337 B2 | 11/2017 | Housman et al. |
| 9,820,789 B2 | 11/2017 | Reiley |
| 9,826,986 B2 | 11/2017 | Donner et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,885 B2 | 3/2019 | Mamo et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| 10,278,737 B2 | 5/2019 | Smith |
| 10,292,778 B2 | 5/2019 | Kostrzewski et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,342,586 B2 | 7/2019 | Schneider |
| 10,349,983 B2 | 7/2019 | Purcell et al. |
| 10,357,287 B2 | 7/2019 | Schlaepfer et al. |
| 10,363,070 B2 | 7/2019 | Jackson et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,426,533 B2 | 10/2019 | Mauldin et al. |
| 10,426,539 B2 | 10/2019 | Schifano et al. |
| 10,433,880 B2 | 10/2019 | Donner et al. |
| 10,478,227 B2 | 11/2019 | Leff et al. |
| 10,492,841 B2 | 12/2019 | Hartdegen et al. |
| 10,492,921 B2 * | 12/2019 | McShane, III ........ A61F 2/4455 |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| 10,555,758 B2 | 2/2020 | Magee et al. |
| 10,588,676 B2 | 3/2020 | Kang et al. |
| 10,588,677 B2 | 3/2020 | McDonnell |
| 10,596,003 B2 | 3/2020 | Donner et al. |
| 10,603,087 B2 | 3/2020 | Brenzel et al. |
| 10,610,275 B2 | 4/2020 | Brianza |
| 10,610,370 B2 | 4/2020 | Baynham |
| 10,617,453 B2 | 4/2020 | Beckett et al. |
| 10,653,454 B2 | 5/2020 | Frey et al. |
| 10,653,544 B2 | 5/2020 | Forsell |
| 10,660,679 B2 | 5/2020 | Kang et al. |
| 10,660,684 B2 | 5/2020 | Kang et al. |
| 10,682,150 B2 | 6/2020 | Stark |
| 10,682,437 B2 | 6/2020 | Roth |
| 10,709,570 B2 * | 7/2020 | Stauffer ................ A61F 2/4455 |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| 10,792,074 B2 | 10/2020 | Jackson |
| 10,799,277 B2 | 10/2020 | Kulper et al. |
| 10,799,367 B2 | 10/2020 | Vrionis et al. |
| 10,842,634 B2 | 11/2020 | Pasini et al. |
| D905,232 S | 12/2020 | Schifano et al. |
| 10,898,333 B2 | 1/2021 | Cordaro |
| 10,932,838 B2 | 3/2021 | Mehl et al. |
| 10,959,758 B2 | 3/2021 | Mesiwala et al. |
| 10,993,757 B2 | 5/2021 | Schifano et al. |
| 11,006,985 B2 | 5/2021 | Caploon et al. |
| D922,568 S | 6/2021 | Schifano et al. |
| 11,071,573 B2 * | 7/2021 | Schneider ............. A61B 17/84 |
| 11,116,519 B2 | 9/2021 | Sand et al. |
| 11,147,591 B2 | 10/2021 | Jackson |
| 11,147,597 B2 | 10/2021 | Jackson |
| 11,147,688 B2 | 10/2021 | Reckling et al. |
| 11,172,939 B2 | 11/2021 | Donner et al. |
| 11,266,767 B2 | 3/2022 | Roth et al. |
| 11,284,798 B2 | 3/2022 | Donner et al. |
| 11,284,887 B2 | 3/2022 | Hartdegen et al. |
| D951,455 S | 5/2022 | Ginn |
| D972,137 S | 12/2022 | Schifano et al. |
| 11,607,251 B2 | 3/2023 | Albert et al. |
| 11,607,256 B1 | 3/2023 | Folsom et al. |
| 11,850,156 B2 | 12/2023 | Mauldin et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |

(56) References Cited

U.S. PATENT DOCUMENTS

| | | |
|---|---|---|
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0071004 A1 | 3/2005 | Re et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1 | 1/2006 | Easley et al. |
| 2006/0025771 A1 | 2/2006 | Jackson |
| 2006/0036247 A1 | 2/2006 | Michelson |
| 2006/0036251 A1 | 2/2006 | Reiley |
| 2006/0036252 A1 | 2/2006 | Baynham et al. |
| 2006/0036322 A1* | 2/2006 | Reiley ............... A61B 17/8625 623/17.11 |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089644 A1 | 4/2006 | Felix |
| 2006/0089656 A1 | 4/2006 | Allard et al. |
| 2006/0095038 A1 | 5/2006 | Jackson |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154314 A1 | 6/2008 | McDevitt |
| 2008/0154374 A1 | 6/2008 | Labrom |
| 2008/0161810 A1 | 7/2008 | Melkent |
| 2008/0161927 A1* | 7/2008 | Savage ............... A61F 2/4455 623/17.16 |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |

(56) References Cited

U.S. PATENT DOCUMENTS

| | | |
|---|---|---|
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0171394 A1 | 7/2009 | Adbou |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thome et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0161061 A1* | 6/2010 | Hunt .................. A61B 17/1604 623/16.11 |
| 2010/0168798 A1 | 7/2010 | Clineff et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0009966 A1 | 1/2011 | Michelson |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1* | 5/2013 | Hunt .................. A61F 2/28 623/23.61 |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1* | 8/2013 | Hunt .................. A61F 2/40 623/23.42 |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0012384 A1 | 1/2014 | Kana et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1* | 5/2014 | Hunt .................. A61F 2/4202 623/17.16 |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |

(56) References Cited

U.S. PATENT DOCUMENTS

| | | | |
|---|---|---|---|
| 2014/0288649 A1 | 9/2014 | Hunt | |
| 2014/0288650 A1 | 9/2014 | Hunt | |
| 2014/0296982 A1 | 10/2014 | Cheng | |
| 2014/0330382 A1 | 11/2014 | Mauldin | |
| 2014/0364917 A1 | 12/2014 | Sandstrom et al. | |
| 2015/0012051 A1 | 1/2015 | Warren et al. | |
| 2015/0039037 A1 | 2/2015 | Donner et al. | |
| 2015/0080951 A1 | 3/2015 | Yeh | |
| 2015/0080972 A1 | 3/2015 | Chin et al. | |
| 2015/0094765 A1 | 4/2015 | Donner et al. | |
| 2015/0112444 A1 | 4/2015 | Aksu | |
| 2015/0147397 A1 | 5/2015 | Altschuler | |
| 2015/0150683 A1 | 6/2015 | Donner et al. | |
| 2015/0173805 A1 | 6/2015 | Donner et al. | |
| 2015/0173904 A1 | 6/2015 | Stark | |
| 2015/0182268 A1 | 7/2015 | Donner et al. | |
| 2015/0190149 A1 | 7/2015 | Assell et al. | |
| 2015/0190187 A1 | 7/2015 | Parent et al. | |
| 2015/0209094 A1 | 7/2015 | Anderson | |
| 2015/0216566 A1 | 8/2015 | Mikhail et al. | |
| 2015/0238203 A1 | 8/2015 | Asfora | |
| 2015/0250513 A1 | 9/2015 | De Lavigne Sainte | |
| 2015/0250611 A1 | 9/2015 | Schifano et al. | |
| 2015/0250612 A1 | 9/2015 | Schifano et al. | |
| 2015/0257892 A1 | 9/2015 | Lechmann et al. | |
| 2015/0282933 A1* | 10/2015 | Hunt | A61F 2/4225 623/16.11 |
| 2015/0313720 A1 | 11/2015 | Lorio | |
| 2015/0320450 A1 | 11/2015 | Mootien et al. | |
| 2015/0320451 A1 | 11/2015 | Mootien et al. | |
| 2015/0320469 A1 | 11/2015 | Biedermann et al. | |
| 2015/0342753 A1 | 12/2015 | Donner et al. | |
| 2016/0000488 A1 | 1/2016 | Cross, III | |
| 2016/0022429 A1 | 1/2016 | Greenhalgh et al. | |
| 2016/0095711 A1 | 4/2016 | Castro | |
| 2016/0095721 A1 | 4/2016 | Schell et al. | |
| 2016/0100870 A1 | 4/2016 | Lavigne et al. | |
| 2016/0106477 A1 | 4/2016 | Hynes et al. | |
| 2016/0106479 A1 | 4/2016 | Hynes et al. | |
| 2016/0120661 A1 | 5/2016 | Schell et al. | |
| 2016/0143671 A1 | 5/2016 | Jimenez | |
| 2016/0016630 A1 | 6/2016 | Papangelou et al. | |
| 2016/0157908 A1 | 6/2016 | Cawley et al. | |
| 2016/0166301 A1 | 6/2016 | Papangelou et al. | |
| 2016/0175113 A1 | 6/2016 | Lins | |
| 2016/0184103 A1 | 6/2016 | Fonte et al. | |
| 2016/0213487 A1 | 7/2016 | Wilson et al. | |
| 2016/0242820 A1 | 8/2016 | Whipple et al. | |
| 2016/0242912 A1 | 8/2016 | Lindsey et al. | |
| 2016/0249940 A1 | 9/2016 | Stark | |
| 2016/0287171 A1 | 10/2016 | Sand et al. | |
| 2016/0287301 A1 | 10/2016 | Mehl et al. | |
| 2016/0310188 A1 | 10/2016 | Marino et al. | |
| 2016/0310197 A1 | 10/2016 | Black et al. | |
| 2016/0324643 A1 | 11/2016 | Donner et al. | |
| 2016/0324656 A1 | 11/2016 | Morris et al. | |
| 2016/0374727 A1 | 12/2016 | Greenhalgh et al. | |
| 2017/0014235 A1 | 1/2017 | Jones et al. | |
| 2017/0020573 A1 | 1/2017 | Cain et al. | |
| 2017/0020585 A1 | 1/2017 | Harshman et al. | |
| 2017/0049488 A1 | 2/2017 | Vestgaarden | |
| 2017/0128214 A1 | 5/2017 | Mayer | |
| 2017/0135733 A1 | 5/2017 | Donner et al. | |
| 2017/0135737 A1 | 5/2017 | Krause | |
| 2017/0143513 A1 | 5/2017 | Sandstrom et al. | |
| 2017/0202511 A1 | 7/2017 | Chang et al. | |
| 2017/0209155 A1 | 7/2017 | Petersen | |
| 2017/0216036 A1 | 8/2017 | Cordaro | |
| 2017/0224393 A1 | 8/2017 | Lavigne et al. | |
| 2017/0246000 A1 | 8/2017 | Pavlov et al. | |
| 2017/0258606 A1* | 9/2017 | Afzal | A61F 2/4465 |
| 2017/0266007 A1 | 9/2017 | Gelaude et al. | |
| 2018/0036041 A1 | 2/2018 | Pham et al. | |
| 2018/0042652 A1 | 2/2018 | Mari et al. | |
| 2018/0042735 A1 | 2/2018 | Schell et al. | |
| 2018/0228617 A1 | 8/2018 | Srour et al. | |
| 2018/0228621 A1 | 8/2018 | Reiley et al. | |
| 2018/0235643 A1 | 8/2018 | Lins et al. | |
| 2018/0256232 A1 | 9/2018 | Russell | |
| 2018/0256351 A1* | 9/2018 | Bishop | A61F 2/4455 |
| 2018/0296227 A1 | 10/2018 | Meek et al. | |
| 2018/0296347 A1 | 10/2018 | Hamzey et al. | |
| 2018/0360512 A1 | 12/2018 | Mari | |
| 2019/0133613 A1 | 5/2019 | Reiley et al. | |
| 2019/0151113 A1* | 5/2019 | Sack | A61F 2/30767 |
| 2019/0159901 A1 | 5/2019 | Mauldin et al. | |
| 2019/0247094 A1 | 8/2019 | Yacoub et al. | |
| 2019/0298528 A1 | 10/2019 | Lindsey et al. | |
| 2019/0298542 A1 | 10/2019 | Kloss | |
| 2019/0343640 A1 | 11/2019 | Donner et al. | |
| 2019/0343641 A1 | 11/2019 | Mauldin et al. | |
| 2019/0343653 A1 | 11/2019 | McKay | |
| 2019/0388228 A1 | 12/2019 | Donner et al. | |
| 2020/0008817 A1 | 1/2020 | Reiley et al. | |
| 2020/0008850 A1 | 1/2020 | Mauldin et al. | |
| 2020/0222195 A1 | 7/2020 | Assell et al. | |
| 2020/0246158 A1 | 8/2020 | Bergey | |
| 2020/0261240 A1 | 8/2020 | Mesiwala et al. | |
| 2020/0268525 A1 | 8/2020 | Mesiwala et al. | |
| 2020/0276019 A1* | 9/2020 | Shetty | B33Y 40/20 |
| 2020/0315647 A1 | 10/2020 | Fojtik et al. | |
| 2020/0315666 A1 | 10/2020 | Nichols et al. | |
| 2020/0345507 A1 | 11/2020 | Reiley | |
| 2020/0345508 A1 | 11/2020 | Reiley | |
| 2020/0345509 A1 | 11/2020 | Reiley | |
| 2020/0345510 A1 | 11/2020 | Reiley | |
| 2021/0153911 A1 | 5/2021 | Stuart et al. | |
| 2021/0169660 A1 | 6/2021 | Reckling et al. | |
| 2021/0212734 A1 | 7/2021 | Mesiwala et al. | |
| 2021/0228360 A1 | 7/2021 | Hunt et al. | |
| 2021/0338454 A1 | 11/2021 | Afzal | |
| 2021/0393408 A1 | 12/2021 | Ginn | |
| 2021/0393409 A1 | 12/2021 | Ginn | |
| 2022/0031474 A1 | 2/2022 | Reckling et al. | |
| 2022/0151668 A1 | 5/2022 | Mauldin et al. | |
| 2022/0273446 A1 | 9/2022 | Stuart et al. | |
| 2022/0273447 A1 | 9/2022 | Ginn | |
| 2022/0273448 A1 | 9/2022 | Ginn et al. | |
| 2022/0280303 A1 | 9/2022 | Mauldin et al. | |
| 2022/0296377 A1 | 9/2022 | Ginn et al. | |
| 2022/0296378 A1 | 9/2022 | Ginn | |
| 2022/0304813 A1 | 9/2022 | Ginn et al. | |
| 2022/0304814 A1 | 9/2022 | Ginn | |
| 2022/0409381 A1 | 12/2022 | Ginn | |
| 2023/0000630 A1 | 1/2023 | Ginn et al. | |
| 2023/0000631 A1 | 1/2023 | Ginn et al. | |
| 2023/0076180 A1 | 3/2023 | Schifano et al. | |
| 2023/0263554 A1 | 8/2023 | Stuart et al. | |
| 2023/0270559 A1 | 8/2023 | Mesiwala et al. | |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| CN | 102429716 A | 5/2012 |
| CN | 104968283 A | 10/2015 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3616634 A1 | 3/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |

(56) References Cited

FOREIGN PATENT DOCUMENTS

| | | |
|---|---|---|
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009000501 A | 1/2009 |
| JP | 2009521990 A | 6/2009 |
| JP | 2009533159 A | 9/2009 |
| JP | 2010137016 A | 6/2010 |
| JP | 2012030105 A | 2/2012 |
| JP | 2014000402 A | 1/2014 |
| JP | 2015510506 A | 4/2015 |
| JP | 2017528251 A | 9/2017 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2006/116850 A1 | 11/2006 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2012/048008 A1 | 4/2012 |
| WO | WO2013/000071 A1 | 1/2013 |
| WO | WO2013/052807 A2 | 4/2013 |
| WO | WO2013/119907 A1 | 8/2013 |
| WO | WO2014/145902 A1 | 9/2014 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.
Khurana et al.; Percutaneous fusion of the sacroiliac joint with hollow modular anchorage screws, clinical and radiological outcome; J Bone Joint Surg; vol. 91-B; No. 5; pp. 627-631; May 2009.
Lu et al.; Mechanical properties of porous materials; Journal of Porous Materials; 6(4); pp. 359-368; Nov. 1, 1999.
Peretz et al.; The internal bony architecture of the sacrum; Spine; 23(9); pp. 971-974; May 1, 1998.
Richards et al.; Bone density and cortical thickness in normal, osteopenic, and osteoporotic sacra; Journal of Osteoporosis; 2010(ID 504078); 5 pgs; Jun. 9, 2010.
Wise et al.; Minimally invasive sacroiliac arthrodesis, outcomes of a new technique; J Spinal Disord Tech; vol. 21; No. 8; pp. 579-584; Dec. 2008.
Mesiwala et al.; U.S. Appl. No. 17/649,265 entitled "Implants for spinal fixation and or fusion," filed Jan. 28, 2022.
Mesiwala et al.; U.S. Appl. No. 17/649,296 entitled "Implants for spinal fixation and or fusion," filed Jan. 28, 2022.
Mauldin et al.; U.S. Appl. No. 17/650,473 entitled "Fenestrated implant," filed Feb. 9, 2022.
Follini et al.; U.S. Appl. No. 17/777,679 entitled "Rod coupling assemblies for bone stabilization constructs," filed May 18, 2022.
Stuart et al.; U.S. Appl. No. 17/812,945 entitled "Sacro-iliac joint stabilizing implants and methods of implantation," filed Jul. 15, 2022.
Mauldin et al.; U.S. Appl. No. 17/805,165 entitled "Systems, device, and methods for joint fusion," filed Jun. 2, 2022.
Mauldin et al.; U.S. Appl. No. 17/822,360 entitled "Fenestrated implant," filed Aug. 25, 2022.
Lindsey et al.; U.S. Appl. No. 18/066,872 entitled "Threaded implants and methods of use across bone segments," filed Dec. 15, 2022.
Reiley et al.; U.S. Appl. No. 18/317,832 entitled "Implants for bone fixation or fusion," filed May 15, 2023.
Stuart et al.; U.S. Appl. No. 18/356,880 entitled "Sacro-iliac join stabilizing implants and methods of implantation," filed Jul. 21, 2023.
Mauldin et al.; U.S. Appl. No. 18/509,864 entitled "Systems, device, and methods for joint fusion," filed Nov. 15, 2023.
Sand et al.; U.S. Appl. No. 18/527,030 entitled "Systems and methods for decorticating the sacroiliac joint," filed Dec. 1, 2023.

\* cited by examiner (Anterior)

(Posterior)

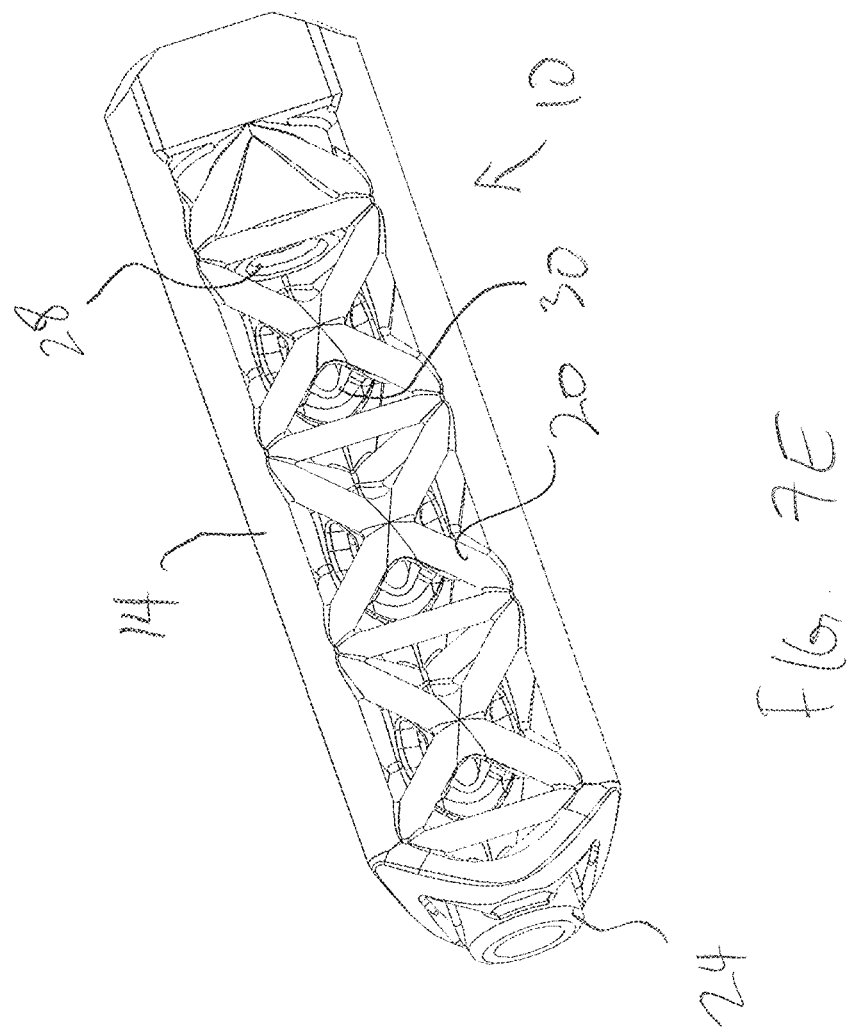

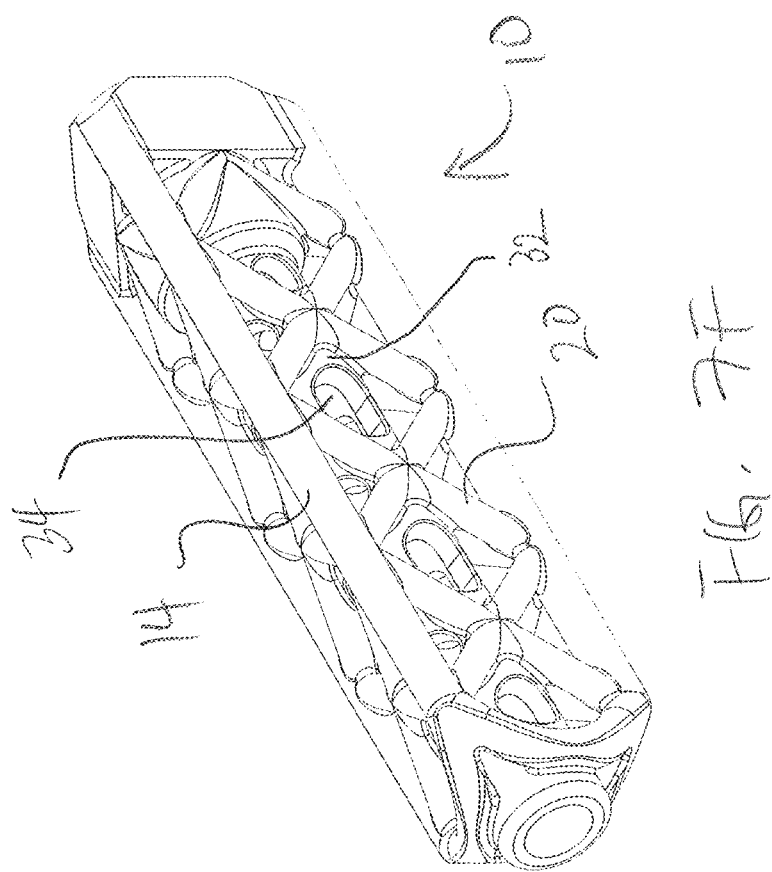

MATRIX IMPLANT

CROSS REFERENCE TO RELATED APPLICATIONS

This application is a continuation of U.S. patent application Ser. No. 16/263,971, filed Jan. 31, 2019, which is a continuation of U.S. patent application Ser. No. 15/593,208, filed May 11, 2017, now U.S. Pat. No. 10,194,962, which is a continuation of U.S. patent application Ser. No. 14/859,005, filed Sep. 18, 2015, now U.S. Pat. No. 9,662,157, which claims priority to U.S. Provisional Patent Application No. 62/052,379, filed Sep. 18, 2014, each of which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to bone implants that can be used to fuse two bone segments together.

BACKGROUND

Many types of hardware are available both for the fixation of bones that are fractured and for the fixation of bones that are to be fused (arthrodesed).

For example, the human hip girdle (see FIGS. 1 and 2) is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and—the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain patients.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion. At the same time the cartilage has to be removed from the "synovial joint" portion of the SI-Joint. This requires a large incision to approach the damaged, subluxed, dislocated, fractured, or degenerated joint. The large incision and removal of tissue can cause significant trauma to the patient, resulting in pain and increasing the time to heal after surgery.

In addition, screw type implants tend to be susceptible to rotation and loosening, especially in joints that are subjected to torsional forces, such as the SI-Joint. Excessive movement of the implant after implantation may result in the failure of the implant to incorporate and fuse with the bone, which may result in the need to remove and replace the failed implant.

Consequently, it would be desirable to provide an implant for bone fusion or fixation that resists rotation, can be implanted using a minimally invasive procedure, and/or that can be used to rescue a failed implant.

SUMMARY OF THE DISCLOSURE

The present invention relates generally to bone implants that can be used to fuse two bone segments together.

In some embodiments, an implant for the fixation or fusion of the SI-Joint is provided. The implant can include an elongate body having a longitudinal axis and a rectilinear cross-sectional profile transverse to the longitudinal axis, the elongate body having a proximal end and a distal end. The elongate body can include a plurality of apex struts aligned with the longitudinal axis and extending between the proximal end and the distal end of the elongate body; a plurality of support struts that extend from one apex strut to another apex strut to form a matrix structure; and a first guide pin receptacle located along the longitudinal axis of the elongate body.

In some embodiments, the rectilinear cross-sectional profile is triangular.

In some embodiments, the rectilinear cross-sectional profile is rectangular or square.

In some embodiments, the elongate body is curved along the longitudinal axis from the proximal end to the distal end of the elongate body. In some embodiments, the elongate body has a curvature between about 5 and 45 degrees.

In some embodiments, the elongate body has a curvature between about 15 and 30 degrees.

In some embodiments, the guide pin receptacle has a circular opening adapted to securely receive a guide pin.

In some embodiments, the elongate body is coated with a titanium plasma spray.

In some embodiments, the elongate body is coated with hydroxyapatite.

In some embodiments, the elongate body is made of metal.

In some embodiments, the metal is titanium.

In some embodiments, the metal comprises a lattice structure.

In some embodiments, the lattice structure is cubic.

In some embodiments, the lattice structure is hexagonal.

In some embodiments, the lattice structure comprises a plurality of beams with a diameter between about 100 to 1000 microns.

In some embodiments, the elongate body is made of a ceramic material.

In some embodiments, the elongate body is mode of a plastic material.

In some embodiments, the elongate body has a porous outer surface.

In some embodiments, all struts are covered in a porous surface.

In some embodiments, all struts are preferentially covered in a porous surface.

In some embodiments, the porous outer surface has a pore size between about 100 to 1000 microns.

In some embodiments, the thickness of the apex struts and the support struts is between about 1 to 5 mm.

In some embodiments, the first guide pin receptacle is located at the distal end of the elongate body.

In some embodiments, the first guide pin receptacle is located at the proximal end of the elongate body.

In some embodiments, the first guide pin receptacle is located at the distal end of the elongate body and a second guide pin receptacle is located at the proximal end of the body.

In some embodiments, the implant can further include a continuous cannula extending between the first guide pin receptacle and the second guide pin receptacle.

In some embodiments, a third guide pin receptacle is located between the first guide pin receptacle and the second guide pin receptacle.

In some embodiments, a plurality of pin receptacles are located between the first guide pin receptacle and the second guide pin receptacle.

In some embodiments, a modular implant for the fixation or fusion of the SI-Joint is provided. The modular implant includes a distal portion comprising a frame, the frame joined to a distal guide pin receptacle and to a plurality of transverse support struts arranged in a rectilinear configuration; a proximal portion comprising a frame joined to a proximal guide pin receptacle and to a plurality of transverse support struts arranged in a rectilinear configuration; and at least one repeating internal portion. The at least one repeating internal portion comprises a plurality of apex struts joined together by oblique support struts arranged in an oblique configuration between the apex struts, a plurality of transverse support struts arranged perpendicularly to the apex struts, the plurality of transverse support struts arranged in a rectilinear configuration at both a proximal end and a distal end of the repeating internal portion, and an internal guide pin receptacle secured to the support struts and aligned with both the distal guide pin receptacle and the proximal guide pin receptacle; wherein the at least one internal repeating portion is positioned between the distal portion and the proximal portion such that the transverse support struts of the distal portion are aligned with a first set of transverse support struts of the repeating internal portion and the transverse support struts of the proximal portion are aligned with the a second set of transverse support struts of the repeating internal portion.

In some embodiments, the oblique supports struts are arranged in an "X" configuration. In some embodiments, the oblique supports struts are arranged in a non-overlapping diagonal configuration.

In some embodiments, the apex and support struts are arranged and spaced to accept bone graft material from the outer surface toward the center of the implant.

In some embodiments, the graft material is autograft.

In some embodiments, the graft material is allograft.

In some embodiments, the graft material is bone morphogenetic protein.

In some embodiments, the implant does not have any struts that extend from the outer surface toward the center of the implant, thereby forming a cavity for receiving a graft material and/or guide pin.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7D-7F illustrate various embodiments of implants having a matrix structure with a plurality of pin receptacles.

DETAILED DESCRIPTION

Figure 1:
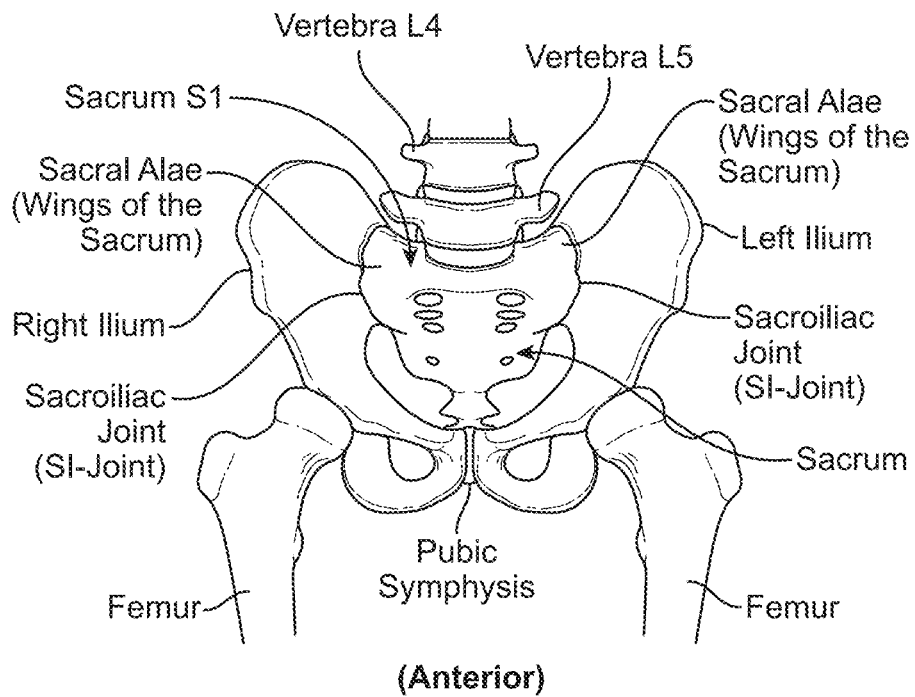
FIGS. 1 and 2 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 2:
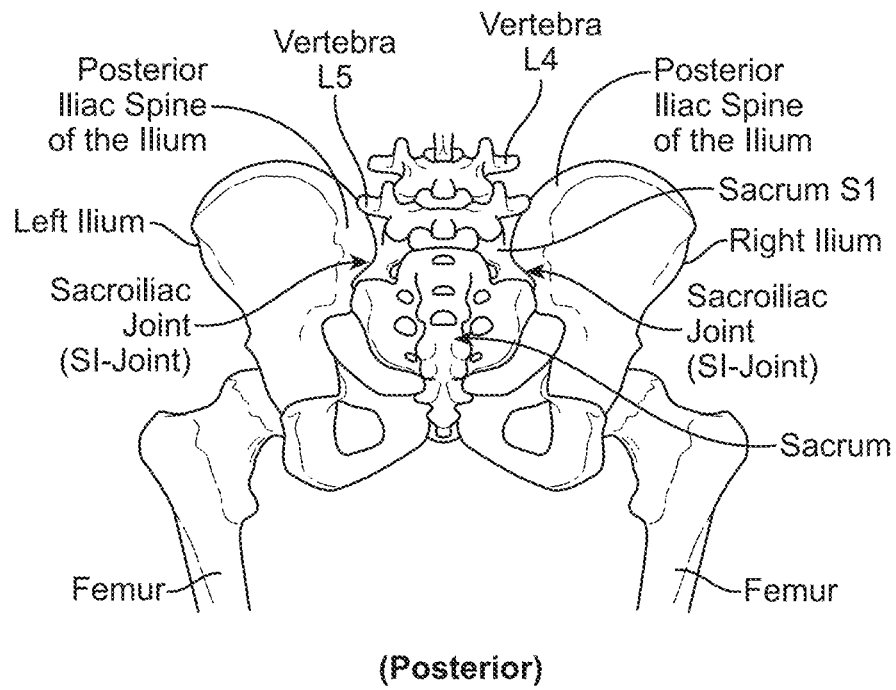
Figures 3, 4:
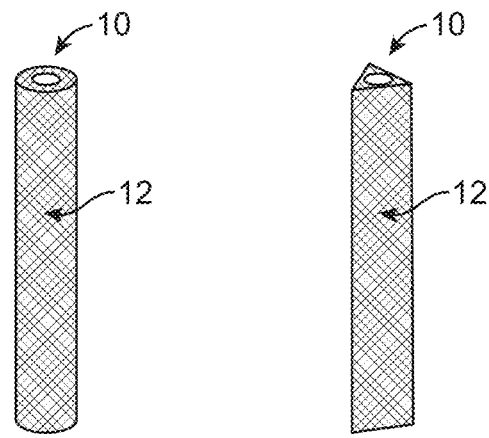
FIGS. 3 and 4 are embodiments of various straight implants that can be used for the fusion or fixation of a joint or two bone segments.

FIG. 3 and FIG. 4 illustrate straight implants 10 with a solid elongate body 12 that can be used for the fixation or fusion of two bone segments. The implant 10 shown in FIG. 3 is cylindrical and can optionally have screw threads along the exterior of the implant body. As mentioned above, cylindrical screw type implants can suffer from excessive rotation. One solution to this problem is the implant 10 in FIG. 4, which has a non-cylindrical cross-sectional area. For example, as shown, the implant 10 can have a triangular cross-sectional area, although other rectilinear cross-sectional profiles may be used as well, including rectangular, hexagonal and the like. Non-cylindrical implants need not have a strict rectilinear cross-sectional profile in order to resist rotation. A cross-sectional area that is non-circular will generally suffice. For example, a tear drop shaped cross-sectional area, or a cross-sectional area with at least one apex, can resist rotation. Other non-circular cross-sectional geometries that may not have a rectilinear component can also work, such as oval cross-sections.

Figure 5:
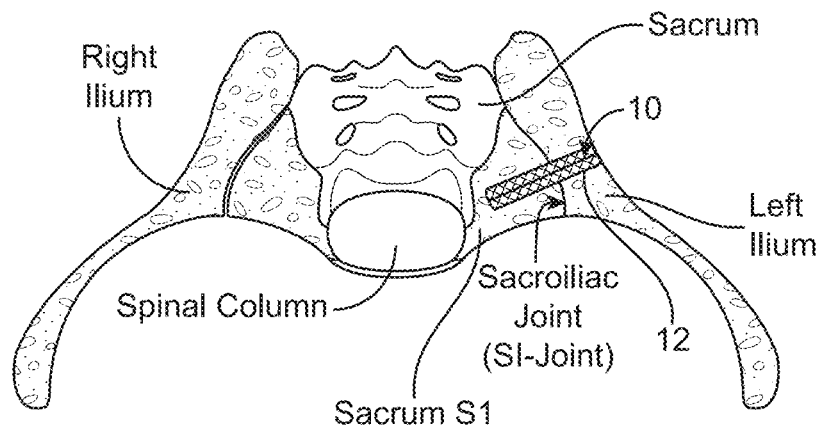
FIG. 5 illustrates an axial section view of the SI-Joint with an implant for the fixation of the SI-Joint using a lateral approach that goes laterally through the ilium, the SI-Joint, and into the sacrum 51.
Figure 6:
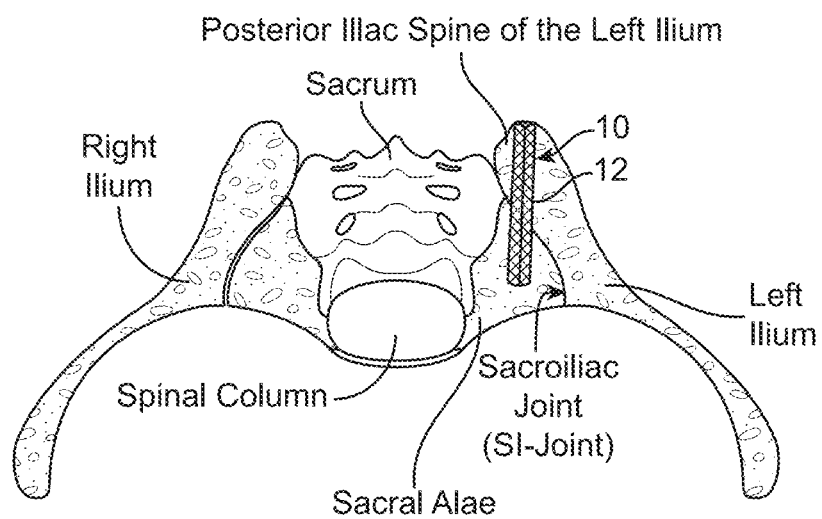
FIG. 6 illustrates an axial section view of the SI-Joint with an implant for the fixation of the SI-Joint using a postero-lateral approach entering from the posterior iliac spine of the ilium, angling through the SI-Joint, and terminating in the sacral alae.

FIG. 5 illustrates insertion of the implant 10 of FIG. 3 or FIG. 4 across the SI-Joint using a lateral approach that goes laterally through the ilium, across the SI-Joint, and into the sacrum. FIG. 6 illustrates insertion of the same implant across the SI-Joint using a postero-lateral approach entering from the posterior iliac spine of the ilium, angling through the SI-Joint, and terminating in the sacral alae. Many of the implants described herein can be inserted across the SI-Joint in a similar manner.

Matrix Implant

In some embodiments, it may be desirable to provide an implant with an open frame structure that can be packed with bone graft material and/or a biologic aid, while providing enough strength to facilitate the fusion of a joint or two bone segments without implant bending or failure.

One way to provide an open frame structure is to construct the elongate body 12 of the implant 10 using a matrix structure, as illustrated in FIGS. 7A-7C and 7G-7I. In some embodiments, each face or side of the elongate body 12 can be constructed using a matrix structure. The implant 10 can have a rectilinear overall cross-sectional profile transverse to a longitudinal axis that extends through the length of the elongate body 12. Each corner or apex of elongate body 12 can be formed with an apex strut 14 that extends between the proximal end 16 and the distal end 18 of the elongate body 12. An implant with a triangular overall cross-sectional profile has three apex struts, while an implant with a square or rectangular overall cross-sectional profile has four apex struts, and so on. To form the faces of the implant, support struts 20 can be arranged in various matrix structures.

Figure 7A:
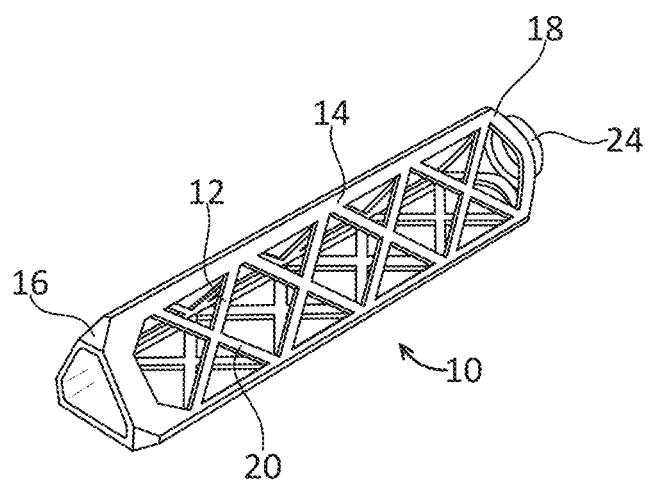
FIGS. 7A-7C illustrate various embodiments of implants having a matrix structure formed from a plurality of struts.

For example, FIG. 7A illustrates one embodiment of a matrix structure where the support struts 20 extend diagonally between two apex struts 14 and cross each other in an "X" configuration such that the support struts 20 define triangular and square openings. Additional transverse support struts that extend between two apex struts at a right angle to both apex struts can also be added. The transverse support struts can be positioned between the "X" support struts and/or can be positioned to cross the middle or intersection of the "X" support struts.

Figure 7B:
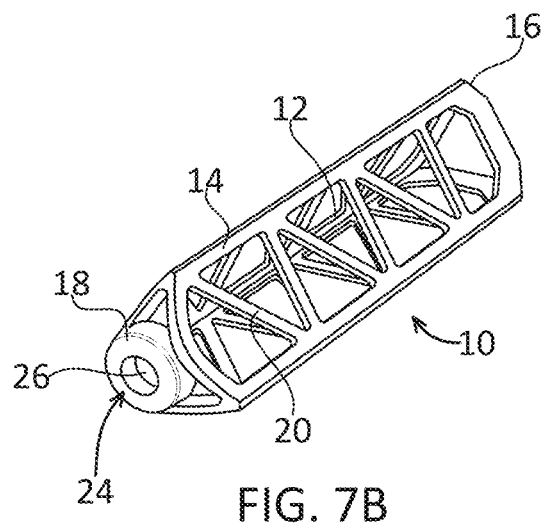

FIG. 7B illustrates another embodiment of a matrix structure where the support struts 20 are arranged in an alternating diagonal and transverse pattern. In this embodiment, the diagonal support struts on one face of the implant are all angled in the same direction such that the diagonal support struts are parallel to each other. The support struts 20 define triangular openings.

Figure 7C:
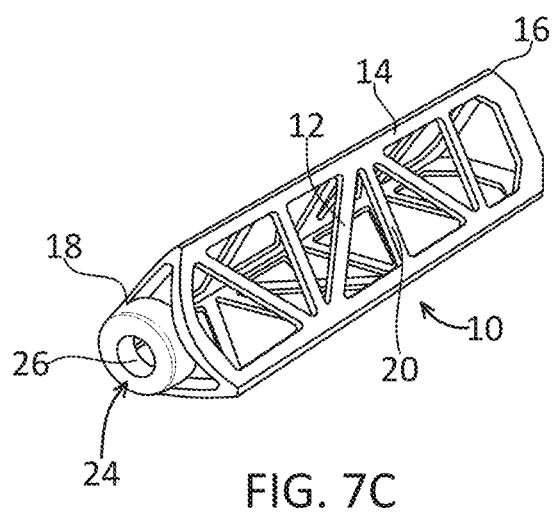

FIG. 7C illustrates yet another embodiment of a matrix structure where the support struts 20 are arranged in an alternating diagonal and transverse pattern. In this embodiment, the diagonal support struts are angled in an alternating pattern such that the diagonal support struts are oriented about 90 degrees to one another to form a zigzag pattern. The support struts 20 also define triangular openings.

The various matrix structures can provide different levels of resistance to various forces that the implant will be subjected to, including compressive, tensile, shear, bending, and torsional forces.

Figure 8:
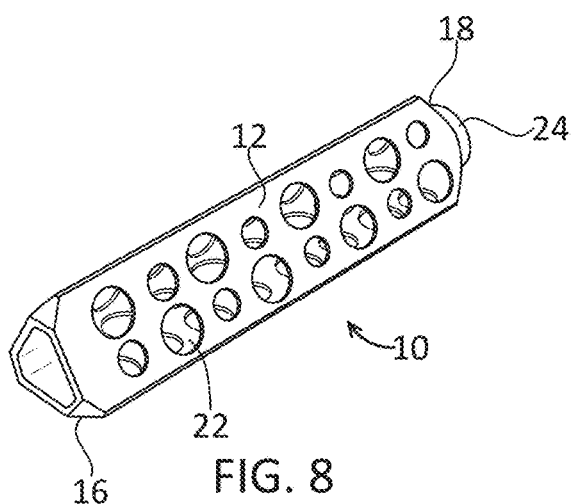
FIG. 8 illustrates an embodiment of a fenestrated implant.

FIG. 8 illustrates an alternative to using a matrix structure to provide openings. The implant 10 can have an elongate body 12 with fenestrations 22. The fenestrations 22 can be circular as shown, and can be of different sizes in, for example, an alternating pattern of large and small fenestrations. The fenestrations 22 can alternatively be rectilinear in shape, such as triangular, square, rectangular, and the like, or curvilinear, such as elliptical, oval, or circular.

In some embodiments, the fenestrations 22 can be triangular, square, rectangular or combinations of the above and can be arranged to form a matrix structure. In other words, the openings in FIGS. 7A-7B defined by the support struts 20 can be considered fenestrations 22.

Figure 7D:
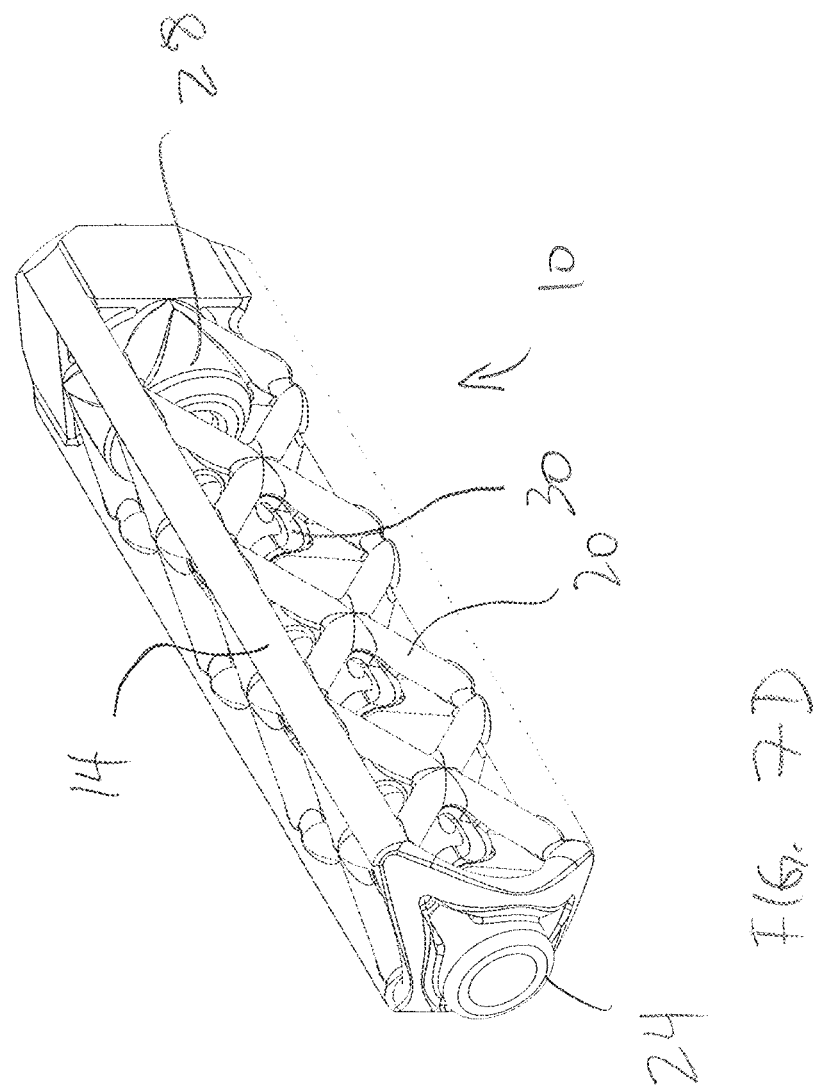
Figure 7G:
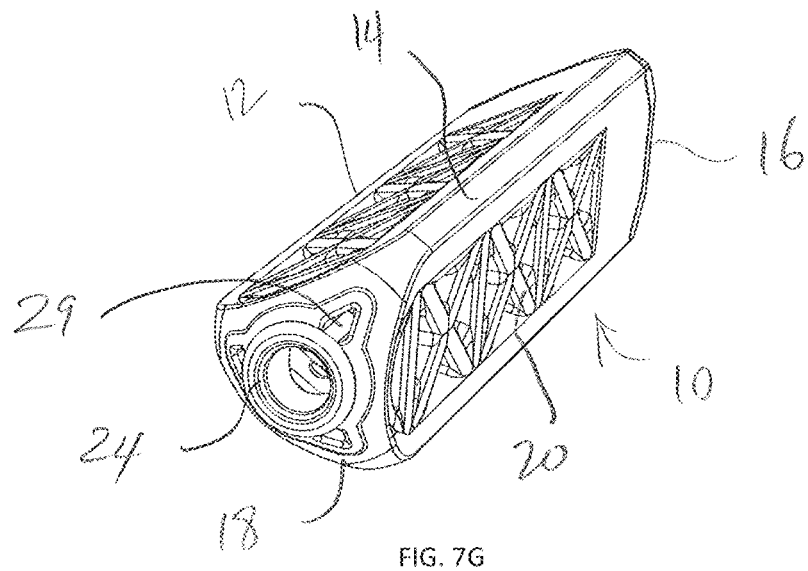
FIGS. 7G-7I illustrate another embodiment of an implant having a matrix structure from various angles and cross-sections.
Figure 7H:
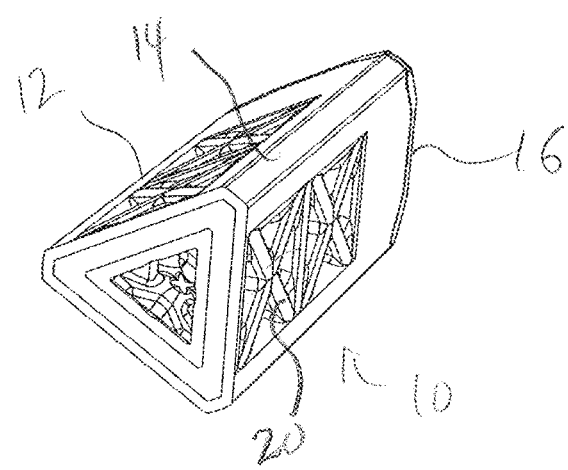
Figure 7I:
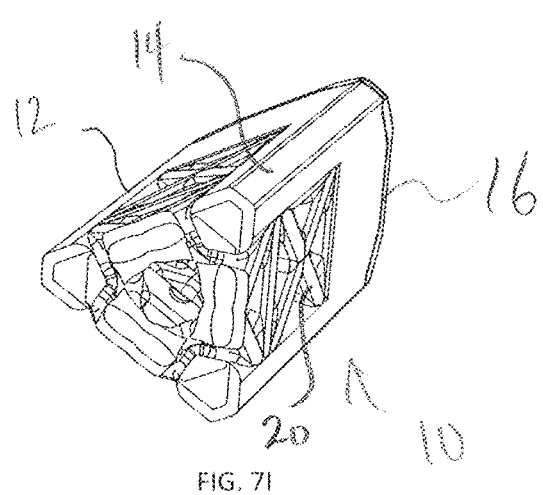

The walls of elongate body 12 can be planar and, as described above, can be formed from support struts 20 and/or fenestrations 22, as shown in FIGS. 7G-7I, for example. Using planar walls to form the elongate body 12 can result in a hollow cavity with the same or similar cross-sectional profile as the overall implant. For example, an implant with a triangular overall cross-sectional profile can also have a cavity with a triangular cross-sectional profile. The thickness of the walls and the apex struts and support struts can be between about 1 mm and 5 mm, or between about 1 and 3 mm. In addition, the distal ends of the walls can be tapered.

To facilitate the use of a traditional guide pin with these implants, the distal end of the implant can include a distal guide pin receptacle 24 with an opening 26 that is sized and shaped to receive a guide pin, as shown in FIGS. 7A-8. For example, the opening 26 can be circular to receive a typical guide pin. In some embodiments, the proximal end can additionally or alternatively have a proximal guide pin receptacle with an opening sized and shaped to receive a guide pin. In some embodiments, a continuous cannula can extend from the proximal guide pin receptacle to the distal guide pin receptacle. In some embodiments, multiple individual and co-linear guide pin receptacles can be present within the implant body between the proximal guide pin receptacle and the distal guide pin receptacle.

For example, FIG. 7D illustrates another embodiment of a matrix structure, similar to the embodiment shown in FIG. 7A, with support struts 20 that extend diagonally between apex struts 14 in an "X" configuration. However, in this embodiment, the implant 10 has a proximal guide pin receptacle 28 located at the proximal end of the implant, a distal guide pin receptacle 24 located at the distal end of the implant, and a plurality of internal guide pin receptacles 30 also located along the longitudinal axis of the implant. The internal guide pin receptacles 30 can be attached to the support struts 20 and/or apex struts 14. As shown, the internal guide pin receptacles 30 are attached at the intersection points of the "X" shaped support struts 20. In addition to receiving the guide pin, the internal guide pin receptacles 30 can provide additional support and bracing to the matrix structure.

FIG. 7E illustrates another embodiment of a matrix structure that is similar to the embodiment shown in FIG. 7D. Both embodiments have "X" shaped support struts 20 and a plurality of internal guide pin receptacles 30. However, this embodiment has additional support struts 20 that extend transversely between the apex struts 14 at right angles. The transverse support struts can be positioned between the "X" shaped support struts as shown, or can be integrated into the "X" shaped support struts. The transverse support struts can provide additional support and bracing to the matrix structure.

FIG. 7F illustrates another embodiment of a matrix structure that is similar to the embodiment shown in FIG. 7D. However, instead of having a plurality of guide pin receptacles, the implant 10 has a single guide pin receptacle 32 that extends from the proximal end to the distal end of the implant. This guide pin receptacle 32 can be a tube or cannula that can be attached to the support struts 20. In some embodiments, the tube or cannula can also have a plurality of fenestrations 34. In some embodiments, the fenestrations 34 can be positioned along the openings of the support struts, which allows the tube to support the support struts 20 while fenestrations promote bony ingrowth and allow the introduction of bone graft material through the implant.

FIGS. 7G-7I illustrates another embodiment of a matrix structure that is similar to the embodiment shown in FIG. 7E. This embodiment also has "X" shaped support struts 20 and additional support struts 20 that extend transversely between the apex struts 14 at right angles. One difference between this embodiment and the embodiment illustrated in FIG. 7E is that the support struts 20 and apex struts 14 in this embodiment have generally rectilinear cross-sectional profiles while the embodiment disclosed in FIG. 7E has generally circular support struts 20 and apex struts 14. In some embodiments, the apex struts 14 can be chamfered to remove sharp edges and the apices of the implant. In addition, this embodiment can have a distal guide pin receptacle 24 and a proximal guide pin receptacle, but unlike some of the embodiments described above, can lack internal guide pin receptacles. The guide pin can instead be supported internally by the inherent cross-sectional geometry of the apex struts and/or support struts. Any of the embodiments herein can have rectilinear, circular, or a combination of the two cross-sectional profiles. The use of the rectilinear struts may allow for the fabrication of the matrix implant by laser cutting a walled structure, while tubular struts may be welded together. A laser cut structure may be structurally stronger than a welded structure, which is important for supporting the large loads applied to the implant after implantation. The distal end 18 of the implant 10 can also have one or more openings 29 that allow graft material to be injected distally through the implant after implantation. In addition, any of the embodiments described herein can optionally have the internal guide pin receptacles, or omit the internal guide pin receptacles. FIG. 7H illustrates a cross-sectional view taken through the transverse struts, while FIG. 7I illustrates a cross-sectional view taken through the "X" shaped support struts.

Figure 9A:
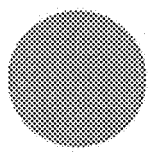
FIGS. 9A-9D illustrate various cross-sectional profiles of the implant microstructure, which can be formed with beam microstructures of varying geometries.
Figure 9B:
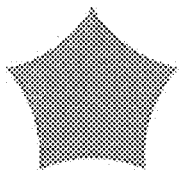
Figure 9C:
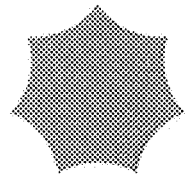
Figure 9D:
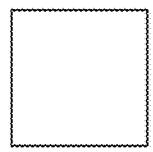

The implant, including the apex struts and/or support struts of the matrix as well as the beams that form the microstructure, can have a variety of shapes. For example, the beams and/or struts can have a cross-section that is rectilinear, curvilinear, or combinations of the two, as illustrated in FIGS. 9A-9D. For example, the beams and/or struts can have a circular cross-section as shown in FIG. 9A, or a curvilinear cross-section as shown in FIGS. 9B and 9C, or a square or rectangular cross section as shown in FIG. 9D. It should be understood that the corners and edges of the beams and/or struts can be rounded off if desired.

Figure 10A:
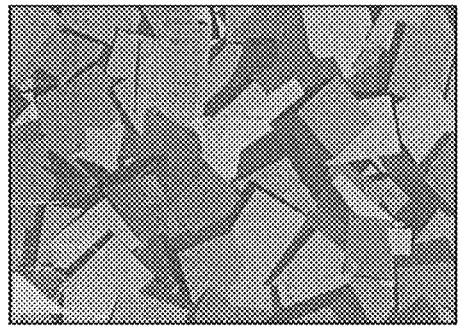
FIGS. 10A-10C illustrate various alternative beam microstructures.
Figure 10B:
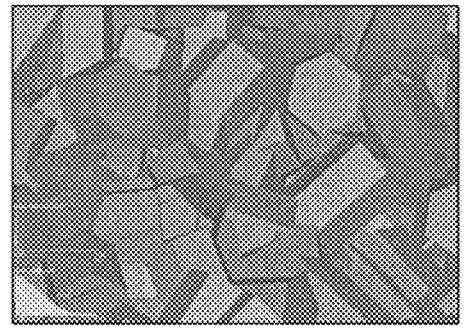
Figure 10C:
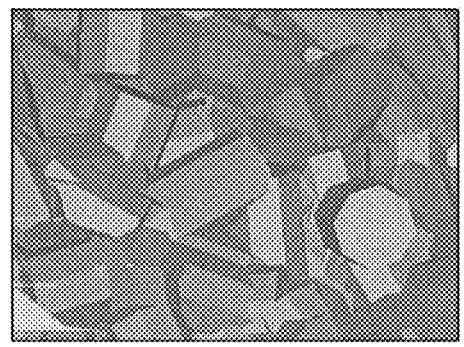
Figure 11A:
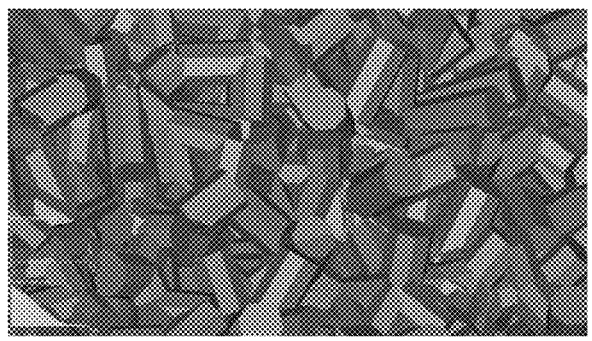
FIGS. 11A-11D illustrate various sizes for the beams that form the implant microstructure.
Figure 11B:
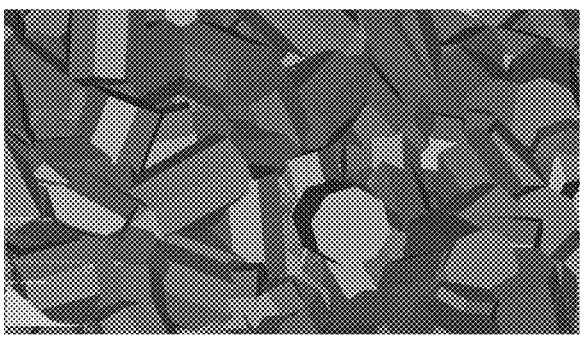
Figure 11C:
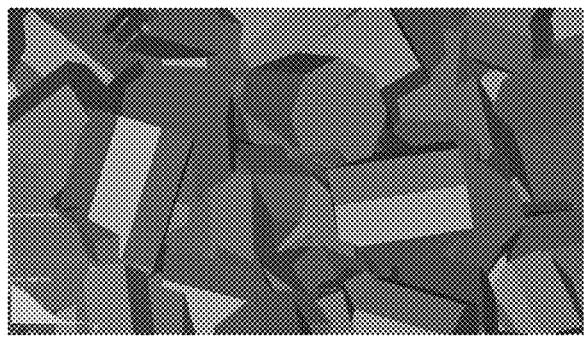
Figure 11D:
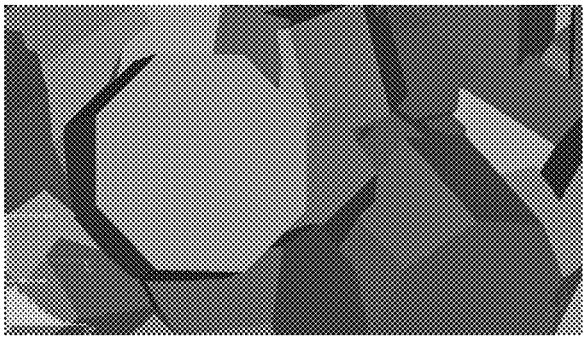

The implant can be made of a variety of materials. For example, the implant can be made of a metal or metal alloy, such as titanium or steel, or a nonmetallic material such as ceramic or polymer. In some embodiments, the implant material can have a certain lattice microstructure formed from the beam microparticles. For example, the lattice microstructure of the apex strut, support struts and other parts of the implant can result in a rough or smooth surface texture, depending on the surface finishing techniques used, such as polishing or application of a metal plasma spray, and the size and shape of the beams that form the lattice microstructure. For example, FIGS. 10A-10C illustrate various beam microstructures that can form the lattice microstructure. FIG. 10A illustrates a cubic beam structure, while FIG. 10B illustrates a hexagonal beam structure, and FIG. 10C illustrates an octagonal beam structure. Other beam structures include tetragonal, rhombohedral, orthorhombic, monoclinic, and triclinic. FIGS. 11A-11D illustrate that the beams can have various sizes. For example, FIGS. 11A-11D illustrate beams having a diameter of about 100, 200 microns, 350 microns, 500 microns, and 1000 microns. In other embodiments, the size of the beam can vary between 50 microns to 5000 microns.

The matrix implant can be manufactured using a variety of techniques. For example, the matrix implant can be 3-D printed using a rapid prototyping technique involving additive manufacturing, such as described in U.S. Patent Publication No. 2010/0161061, which is herein incorporated by reference in its entirety for all purposes. The 3-D printed matrix implant can be made of a metal, polymer, or ceramic material. For example, a metal powder such as titanium powder can be fused together to form the implant structure. Other techniques include cutting out the fenestrations or openings, using a laser for example, to form the apex struts and support struts, or using electric discharge machining (EDM) to create the matrixes or fenestrations.

3-D printing allows the porosity of the implant to be controlled. For example, the implant can have a volume porosity between about 30 and 70 percent, with an average pore size between 100 and 1000 microns. The pores can be largely interconnected, largely unconnected, or a mix of interconnected and unconnected pores. In some embodiments, the pores can be located throughout the material of the implant, including the apex struts and support struts, and on all or some of the strut surfaces, including the inner and outer implant surfaces. For example, the fusion of the beam microparticles to form the struts can result in a porous, semi-porous, or nonporous structure, depending on the degree of fusion between the beam microparticles. In other embodiments, the pores can be located in a porous coating that can be applied onto the implant. For example, a porous coating can be applied using a titanium plasma spray process, or another metal plasma spray process. The coating can be applied to the outer surfaces of the implant, the interior surfaces of the implant, or both the outer and interior surfaces of the implant. For example, the coating could be preferentially applied to the outer surface of a matrixed implant to provide bony ingrowth and ongrowth, and not applied to the inner portion of the implant to maximize bony through-growth within the implant. Also, the coating can be applied preferentially from proximal to distal, or vice versa. The thickness of a porous coating can be between about 500 and 1,500 microns. In addition or alternatively to the porous metal coating, a hydroxyapatite coating can also be applied to the implant. In some embodiments, the porosity can be varied along the length of the implant. In some embodiments, the thickness of the coating can be varied along the length of the implant. In some embodiments, the thickness of the coating applied to the outer surface can be different than the thickness of the inner coating. For example, the outer coating may be greater than the inner coating in some embodiments. In other embodiments, the thickness of the inner and outer coatings can be the same.

Figure 12:
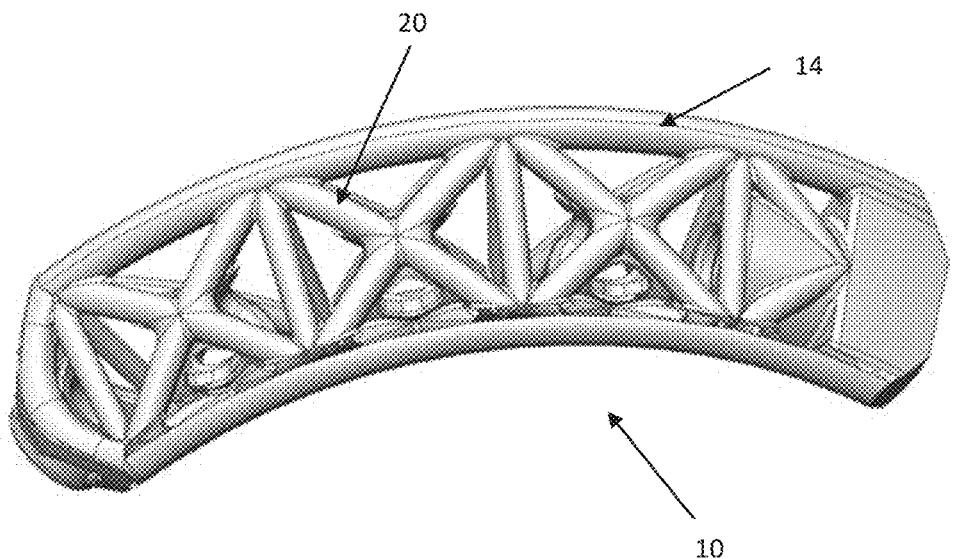
FIG. 12 illustrates an embodiment of a curved matrix implant.

In some embodiments, as illustrated in FIG. 12, the apex struts 14 can be curved from the proximal end to the distal end of the apex strut 14, thereby resulting in a curved matrix implant 10 similar to the curved implants described in co-pending U.S. Provisional Application No. 62/052,318, filed Sep. 18, 2014 and entitled "IMPLANTS FOR BONE FIXATION OR FUSION," which is herein incorporated by reference in its entirety for all purposes.

Figure 13:
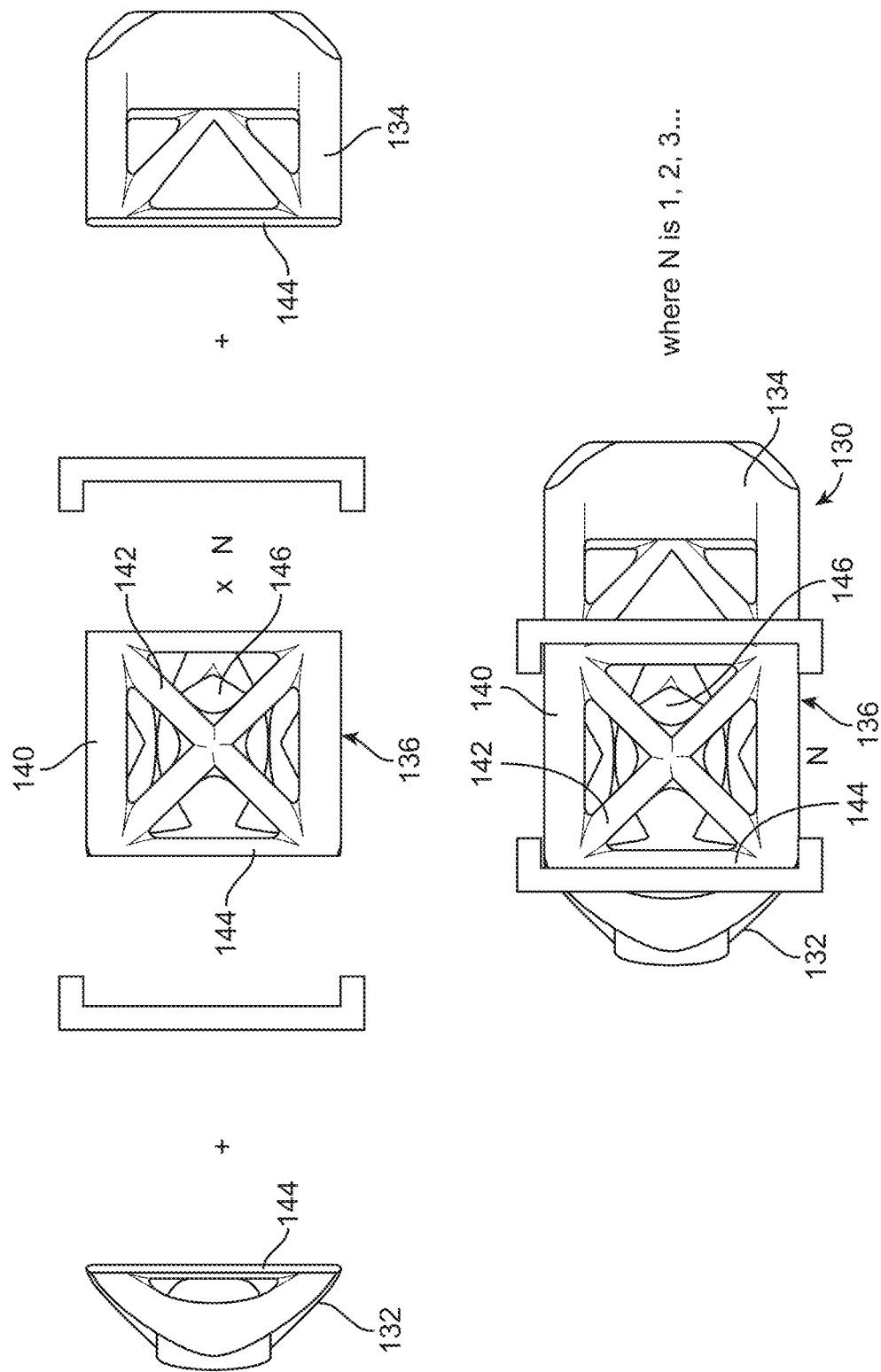
FIG. 13 illustrates an embodiment of a modular matrix implant.

The length of the implant can vary between about 25 to 95 mm. The matrix structure can be modular, as shown in FIG. 13, which allows the length of the implant to be varied by the addition of additional repeating subunits during the design and/or fabrication of the implant. For example, the modular matrix implant 130 can have a distal end portion 132, a proximal end portion 134, and one or more repeating internal portions 136. The distal end portion 132 can have a distal guide pin receptacle 138, and the proximal end portion 134 can have a proximal guide pin receptacle 136, much like the embodiments discussed above. The repeating internal portion 136 can have apex struts 140 and support struts 142, as described above. For example, as shown, the support struts 142 can have an "X" configuration and can be located between two transverse support struts 144. The two transverse support struts 144 can be half the normal transverse support struts such that when two repeating internal portions 136 are joined together, the two half support struts merge to form a whole transverse support strut. The proximal and distal end portions 132, 134 can also have a coupling portion that is formed from half transverse support struts 144 that can be merged with the half transverse support struts 144 of the repeating internal portion 136. In some embodiments, the repeating internal portion 136 can also have an internal guide pin receptacle 146

In some embodiments, the length of the repeating internal portion 136 can be about 10 mm. In other embodiments, the length can be between about 5 and 25 mm. In some embodiments, the repeating internal portion 136 can have support struts that form half an "X", such that the repeating internal portions are arranged in an alternating pattern to form "X" shaped support struts. In some embodiments, the support struts are simply diagonal struts that extend across the length of the repeating internal portion.

Methods of Implantation

The methods of implantation of the various implants described herein are described in U.S. Patent Publication No. 2011/0087294, U.S. Pat. Nos. 8,425,570, 8,444,693, 8,414,648, and 8,470,004, and co-pending U.S. Provisional Application No. 61/891,326, each of which is herein incorporated by reference in its entirety for all purposes. These methods are particularly suited for use with straight implants.

The curved implant illustrated in FIG. 12 may require modifications to the method of insertion protocols. Because the implant is curved, it may not be possible or desirable to attempt to hammer or tap the implant into the bone along a straight path using a straight guide pin, a straight drill, a straight broach and the like. Instead, it may be desirable to create and form a curved insertion path that matches the curvature of the implant.

For example, the tooling used to create the curved insertion path can have a radius of curvature that matches the radius of curvature of the implant. For example, some or all of the tooling and the implant can have a matching radius of curvature. The tooling, which can include a guide pin, a tool guide, a drill bit, a broach, and impact hammer and the like can be rotatably secured by an arm with a length equal to the radius of curvature, with one end of the arm attached to a pivot and the other end used to secure the tools and/or implant.

The rotating arm can be used to drive a curved guide pin into the bone to create a curved path through the bone, such as the ilium and the sacrum. A relatively short drill bit with a lumen for receiving the guide pin can be disposed over the curved guide pin to drill out a curved pilot bore. In some embodiments, the drill bit can be secured by the pivoting arm at the end of a curved guide and can be used to drill the curved pilot bore without the insertion of the curved guide pin.

For a curved implant with a circular cross section, the curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

For a rectilinear implant or more broadly a noncircular implant, the curved pilot bore can be shaped using an appropriately shaped broach that matches the overall cross-sectional shape of the implant. A curved broach, or a short broach, can be advanced over the curved guide pin if present, otherwise the curved broach or short broach can be held in the pivoting arm and advanced through the pilot bore by rotation of the pivoting arm. As the broach is advanced, it shapes the pilot bore into a shape that matches the shape of the implant.

The curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

More generally, the implants described herein can be used to fuse any two bone segments, such as two bones that form a joint or two bones resulting from a fracture.

The terms "about" and "approximately" and the like can mean within 5, 10, 15, 20, 25, or 30 percent.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. An implant for the fixation or fusion of a sacroiliac joint, the implant comprising:
    an elongate body having a fixed length, a proximal end, a distal end, a longitudinal axis and a rectilinear outer profile in a cross-section transverse to the longitudinal axis, the elongate body further comprising:
    a plurality of linear apex struts disposed between the proximal end and the distal end of the elongate body, wherein each apex strut of the plurality of linear apex struts is part of a first pair of apex struts with a first circumferentially adjacent apex strut, and is part of a second pair of apex struts with a second circumferentially adjacent apex strut, and
    a plurality of faces, wherein every pair of circumferentially adjacent linear apex struts has one of the plurality of faces therebetween, and wherein each of the plurality of faces includes a plurality of fenestrations,
        wherein the plurality of linear apex struts are preferentially porous with radially outer portions of the plurality of linear apex struts being porous and radially inner portions of the plurality of linear apex struts are not porous.

2. The implant of claim 1, wherein each of the plurality of faces comprises a matrix structure.

3. The implant of claim 1, wherein each of the plurality of faces comprises a matrix structure including a plurality of support struts extending between the respective pair of adjacent linear apex struts.

4. The implant of claim 3, wherein the plurality of support struts comprises a plurality of transverse support struts.

5. The implant of claim 3, wherein the plurality of support struts comprises a plurality of oblique support struts.

6. The implant of claim 3, wherein the plurality of support struts are preferentially porous with radially outer portions of the plurality of support struts being porous and radially inner portions of the plurality of support struts not porous.

7. The implant of claim 1, wherein each face includes a first set of fenestrations and a second set of fenestrations, wherein the fenestrations in the first set of fenestrations have a different size than the fenestrations in the second set of fenestrations.

8. The implant of claim 7, wherein the fenestrations in the first set of fenestrations are triangular.

9. An implant for the fixation or fusion of a sacroiliac joint, the implant comprising:
an elongate body having a fixed length, a proximal end, a distal end, a longitudinal axis and a rectilinear outer profile in a cross-section transverse to the longitudinal axis, the elongate body further comprising:
a plurality of linear apex struts parallel with the longitudinal axis and disposed between the proximal end and the distal end of the elongate body,
wherein each apex strut of the plurality of linear apex struts is part of a first pair of apex struts with a first circumferentially adjacent apex strut, and is part of a second pair of apex struts with a second circumferentially adjacent apex strut; and
a plurality of faces, wherein every pair of circumferentially adjacent linear apex struts has one of the plurality of faces therebetween, and wherein each of the plurality of faces includes a plurality of support struts defining a plurality of fenestrations,
wherein the plurality of linear apex struts are preferentially porous with radially outer portions of the plurality of linear apex struts being porous and radially inner portions of the plurality of linear apex struts are not porous.

10. The implant of claim 9, wherein the plurality of support struts in each of the plurality of faces includes at least one of a plurality of transverse support struts or a plurality of oblique support struts.

11. The implant of claim 10, wherein the plurality of support struts in each of the plurality of faces consists of a plurality of transverse support struts and a plurality of oblique support struts.

12. The implant of claim 9, wherein each face of the plurality of faces includes a first set of fenestrations and a second set of fenestrations, wherein the fenestrations in the first set of fenestrations have a different size than the fenestrations in the second set of fenestrations.

13. The implant of claim 12, wherein the fenestrations in the first set of fenestrations are triangular.

14. An implant for the fixation or fusion of a sacroiliac joint, the implant comprising:
an elongate body having a fixed length, a proximal end, a distal end, a longitudinal axis and a triangular outer profile in a cross-section transverse to the longitudinal axis, the elongate body further comprising:
a plurality of linear apex struts disposed between the proximal end and the distal end of the elongate body,
wherein each apex strut of the plurality of linear apex struts is part of a first pair of apex struts with a first circumferentially adjacent apex strut, and is part of a second pair of apex struts with a second circumferentially adjacent apex strut; and
a plurality of faces, wherein every pair of circumferentially adjacent linear apex struts has one of the plurality of faces therebetween, and wherein each of the plurality of faces includes a plurality of support struts forming a plurality of fenestrations in the corresponding face,
wherein the plurality of linear apex struts are preferentially porous with radially outer portions of the plurality of linear apex struts being porous and radially inner portions of the plurality of linear apex struts are not porous, and
wherein the plurality of support struts in each of the plurality of faces are preferentially porous with radially outer portions of the plurality of support struts being porous and radially inner portions of the plurality of support struts not porous.

15. The implant of claim 14, wherein the plurality of support struts in each of the plurality of faces includes at least one of a plurality of transverse support struts or a plurality of oblique support struts.

16. The implant of claim 15, wherein the plurality of support struts in each of the plurality of faces consists of a plurality of transverse support struts and a plurality of oblique support struts.

17. The implant of claim 14, wherein each face of the plurality of faces includes a first set of fenestrations and a second set of fenestrations, wherein the fenestrations in the first set of fenestrations have a different size than the fenestrations in the second set of fenestrations.

18. The implant of claim 17, wherein the fenestrations in the first set of fenestrations are triangular.

* * * * *